US008513302B2

(12) United States Patent
Hammock et al.

(10) Patent No.: US 8,513,302 B2
(45) Date of Patent: *Aug. 20, 2013

(54) REDUCING NEPHROPATHY WITH INHIBITORS OF SOLUBLE EPOXIDE HYDROLASE AND EPOXYEICOSANOIDS

(75) Inventors: Bruce D. Hammock, Davis, CA (US); Takaho Watanabe, Hadano (JP); Seung-Jin Ma, Mokpo (KR); Susan E. Bennett, Davis, CA (US); Judith S. Stern, Davis, CA (US); Christophe Morisseau, West Sacramento, CA (US); In-Hae Kim, Matsuyama-si (JP)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/100,978

(22) Filed: May 4, 2011

(65) Prior Publication Data

US 2011/0269831 A1 Nov. 3, 2011

Related U.S. Application Data

(63) Continuation of application No. 11/719,092, filed as application No. PCT/US2005/008765 on Mar. 16, 2005, now abandoned, application No. 13/100,978, which is a continuation-in-part of application No. 12/396,391, filed on Mar. 2, 2009, which is a continuation of application No. 10/817,334, filed on Apr. 2, 2004, now abandoned.

(60) Provisional application No. 60/553,847, filed on Mar. 16, 2004, provisional application No. 60/460,559, filed on Apr. 3, 2003.

(51) Int. Cl.
*A61K 31/17* (2006.01)
*A61K 31/16* (2006.01)

(52) U.S. Cl.
USPC ............ 514/475; 514/588; 514/546; 514/613

(58) Field of Classification Search
USPC ................... 514/475, 588, 476, 613
See application file for complete search history.

(56) References Cited

U.S. PATENT DOCUMENTS

| | | |
|---|---|---|
| 3,539,626 A | 11/1970 | Gagneux |
| 3,587,060 A | 6/1971 | Quinn et al. |
| 3,703,537 A | 11/1972 | Richter et al. |
| 3,755,415 A | 8/1973 | Richter et al. |
| 4,252,954 A | 2/1981 | Abdulla et al. |
| 5,037,826 A | 8/1991 | Blythin et al. |
| 5,142,017 A | 8/1992 | Sugimoto et al. |
| 5,231,216 A | 7/1993 | Pecar et al. |
| 5,273,982 A | 12/1993 | Alig et al. |
| 5,314,902 A | 5/1994 | Tjoeng et al. |
| 5,389,682 A | 2/1995 | Tait et al. |
| 5,445,956 A | 8/1995 | Hammock et al. |
| 5,576,335 A | 11/1996 | Sueda et al. |
| 5,614,498 A | 3/1997 | Ishikawa et al. |
| 5,637,113 A | 6/1997 | Tartaglia et al. |
| 5,877,224 A | 3/1999 | Brocchini et al. |
| 5,886,044 A | 3/1999 | Widdowson et al. |
| 5,962,455 A | 10/1999 | Blum et al. |
| 6,150,415 A | 11/2000 | Hammock et al. |
| 6,287,285 B1 | 9/2001 | Michal et al. |
| 6,290,722 B1 | 9/2001 | Wang |
| 6,299,604 B1 | 10/2001 | Ragheb et al. |
| 6,322,847 B1 | 11/2001 | Zhong et al. |
| 6,326,141 B1 | 12/2001 | Kahn et al. |
| 6,329,395 B1 | 12/2001 | Dugar et al. |
| 6,335,029 B1 | 1/2002 | Kamath et al. |
| 6,344,358 B1 | 2/2002 | Matsuoka et al. |
| 6,351,506 B1 | 2/2002 | Lewicki |
| 6,444,686 B1 | 9/2002 | Ko et al. |
| 6,444,691 B1 | 9/2002 | Oremus et al. |
| 6,531,506 B1 * | 3/2003 | Kroetz et al. ............... 514/475 |
| 6,562,849 B1 | 5/2003 | Fujita et al. |
| 6,586,446 B1 | 7/2003 | Santella, III et al. |
| 6,613,572 B2 | 9/2003 | Matsuoka et al. |
| 6,710,043 B1 | 3/2004 | Yamada et al. |

(Continued)

FOREIGN PATENT DOCUMENTS

| | | |
|---|---|---|
| CA | 2 360 360 A1 | 7/2000 |
| DE | 3540919 A1 | 5/1987 |

(Continued)

OTHER PUBLICATIONS

Eipstein et al (Hypertension (1992) 19:403-418).*
PCT International Search Report dated Aug. 1, 2007 issued in PCT/US2005/008765.
PCT International Preliminary Report on Patenability and Written Opinion dated Aug. 21, 2007 issued in PCT/US2005/008765.
U.S. Office Action dated Jul. 14, 2010 issued in U.S. Appl. No. 11/719,092.
U.S. Office Action dated Feb. 4, 2011 issued in U.S. Appl. No. 11/719,092.
U.S. Office Action (Board of Patent Appeals and Interferences Decision on Appeal) dated Jun. 22, 2010 issued in U.S. Appl. No. 10/694,641.
U.S. Office Action dated Jan. 7, 2007 issued in U.S. Appl. No. 10/817,334.
U.S. Final Office Action dated Feb. 13, 2008 issued in U.S. Appl. No. 10/817,334.

(Continued)

Primary Examiner — Shirley V Gembeh

(74) Attorney, Agent, or Firm — Jennifer L. Wahlsten; Weaver Austin Villeneuve & Sampson LLP

(57) ABSTRACT

The invention provides uses and methods for reducing nephropathy in persons with diabetes mellitus (particularly Type 2 diabetes), in persons with metabolic syndrome, in persons with triglyceride levels over 215 mg/dL, and in persons with a cholesterol level over 200 mg/dL, by administering an inhibitor of soluble epoxide hydrolase ("sEH"). Optionally, a cis-epoxyeicosantrienoic acid ("EET") can be administered with the sEH inhibitor. The invention further provides for using EETs in conjunction with one or more sEH inhibitors to reduce hypertension, and for compositions of EETs coated with a material insoluble in an acid of pH 3 but soluble in a solution with a pH of 7.4 or higher.

20 Claims, No Drawings

(56) References Cited

U.S. PATENT DOCUMENTS

| | | |
|---|---|---|
| 6,831,082 B2 | 12/2004 | Ingraham et al. |
| 7,176,201 B2 | 2/2007 | Piomelli et al. |
| 7,662,910 B2 | 2/2010 | Hammock et al. |
| 8,188,289 B2 | 5/2012 | Hammock et al. |
| 8,263,651 B2 | 9/2012 | Hammock et al. |
| 2002/0045548 A1 | 4/2002 | Saito |
| 2002/0077355 A1 | 6/2002 | Liao et al. |
| 2002/0090732 A1 | 7/2002 | Matsuoka et al. |
| 2003/0022929 A1 | 1/2003 | Ingraham et al. |
| 2003/0078426 A1 | 4/2003 | Fujita et al. |
| 2003/0139469 A1 | 7/2003 | Weiss et al. |
| 2004/0014745 A1 | 1/2004 | Yamada et al. |
| 2004/0014754 A1 | 1/2004 | Crooks et al. |
| 2004/0054187 A1 | 3/2004 | Mammen et al. |
| 2004/0092487 A1 | 5/2004 | Kroetz et al. |
| 2004/0092567 A1 | 5/2004 | Ingraham et al. |
| 2005/0026844 A1* | 2/2005 | Hammock et al. ............... 514/18 |
| 2005/0164951 A1 | 7/2005 | Hammock et al. |
| 2005/0203135 A1 | 9/2005 | Burdick et al. |
| 2007/0054904 A1 | 3/2007 | Knolle et al. |
| 2007/0225283 A1 | 9/2007 | Hammock et al. |
| 2009/0018092 A1 | 1/2009 | Hammock et al. |
| 2009/0326039 A1 | 12/2009 | Hammock et al. |
| 2011/0021448 A1 | 1/2011 | Hammock et al. |
| 2011/0269831 A1 | 11/2011 | Hammock et al. |

FOREIGN PATENT DOCUMENTS

| | | |
|---|---|---|
| DO | 123 466 A | 12/1976 |
| EP | 0 503 627 A1 | 9/1992 |
| EP | 1 031 564 A1 | 8/2000 |
| EP | 1 167 366 A1 | 1/2002 |
| GB | 1 287 317 | 8/1972 |
| JP | 49-116004 A | 11/1974 |
| JP | 49-048548 B | 12/1974 |
| JP | 63-159382 A | 7/1988 |
| JP | H04-13666 A | 1/1992 |
| JP | H07-133224 A | 5/1995 |
| JP | 2007-258199 A | 10/1995 |
| JP | 9160300 A | 6/1997 |
| JP | 2001-158789 A | 6/2001 |
| JP | 2002-059655 A | 2/2002 |
| JP | 2002-506058 A | 2/2002 |
| JP | 2002-509881 A | 4/2002 |
| JP | 2002-179568 A | 6/2002 |
| JP | 2002-532427 A | 10/2002 |
| JP | 2003-501473 A | 1/2003 |
| JP | 2003-512355 A | 4/2003 |
| JP | 2003-522120 T | 7/2003 |
| JP | 2004-002414 A | 1/2004 |
| JP | 2005-539072 A | 12/2005 |
| JP | 2006-511484 A | 4/2006 |
| JP | 2006-525327 | 11/2006 |
| JP | 2007-503393 A | 2/2007 |
| JP | 2010-500959 A | 1/2010 |
| JP | 2011-509838 A | 3/2011 |
| RU | 2 208 608 C2 | 7/2003 |
| WO | WO 95/33729 A1 | 12/1995 |
| WO | WO 96/40258 A1 | 12/1996 |
| WO | WO 98/06261 A1 | 2/1998 |
| WO | WO 99/07700 A1 | 2/1999 |
| WO | WO 99/09024 A1 | 2/1999 |
| WO | WO 99/15164 | 4/1999 |
| WO | WO 99/32437 A1 | 7/1999 |
| WO | WO 99/46244 A1 | 9/1999 |
| WO | WO 02/14311 A2 | 2/2000 |
| WO | WO 00/02306 * | 4/2000 |
| WO | WO 00/23060 | 4/2000 |
| WO | WO 00/42011 A1 | 7/2000 |
| WO | WO 00/48593 A1 | 8/2000 |
| WO | WO 00/61581 A1 | 10/2000 |
| WO | WO 00/72834 A2 | 12/2000 |
| WO | WO 00/72834 A3 | 12/2000 |
| WO | WO 00/76457 A2 | 12/2000 |
| WO | WO 00/76457 A3 | 12/2000 |
| WO | WO 01/28987 | 4/2001 |
| WO | WO 01/42212 A1 | 6/2001 |
| WO | WO 02/14311 A3 | 2/2002 |
| WO | WO 03/002555 | 1/2003 |
| WO | WO 03/009845 A1 | 2/2003 |
| WO | WO 03/061597 | 7/2003 |
| WO | WO 03/070242 A1 | 8/2003 |
| WO | WO 03/070691 A1 | 8/2003 |
| WO | WO 03/070727 A1 | 8/2003 |
| WO | WO 03/076426 A2 | 9/2003 |
| WO | WO 03/076426 A3 | 9/2003 |
| WO | WO 03/077907 A1 | 9/2003 |
| WO | WO 03/082861 A2 | 10/2003 |
| WO | WO 03/082861 A3 | 10/2003 |
| WO | WO 03/097586 A1 | 11/2003 |
| WO | WO 03/097618 A1 | 11/2003 |
| WO | WO 03/099805 | 12/2003 |
| WO | WO 2004/007459 A2 | 1/2004 |
| WO | WO 2004/007459 A3 | 1/2004 |
| WO | WO 2004/026836 A2 | 4/2004 |
| WO | WO 2004/026836 A3 | 4/2004 |
| WO | WO 2004/063181 A1 | 7/2004 |
| WO | WO 2004/064730 A2 | 8/2004 |
| WO | WO 2004/064730 A3 | 8/2004 |
| WO | WO 2004/089296 | 10/2004 |
| WO | WO 2004/094381 A1 | 11/2004 |
| WO | WO 2004/111009 A1 | 12/2004 |
| WO | WO 2004/111031 A1 | 12/2004 |
| WO | WO 2005/014580 A1 | 2/2005 |
| WO | WO 2005/018624 A2 | 3/2005 |
| WO | WO 2005/030209 A1 | 4/2005 |
| WO | WO 2005/037199 A2 | 4/2005 |
| WO | WO 2005/037199 A3 | 4/2005 |
| WO | WO 2005/089380 | 9/2005 |
| WO | WO 2005/089763 A1 | 9/2005 |
| WO | WO 2005/105802 | 11/2005 |
| WO | WO 2005/113511 A1 | 12/2005 |
| WO | WO 2006/009741 A1 | 1/2006 |
| WO | WO 2006/014136 A1 | 2/2006 |
| WO | WO 2006/014359 A2 | 2/2006 |
| WO | WO 2006/014359 A3 | 2/2006 |
| WO | WO 2006/016039 A1 | 2/2006 |
| WO | WO 2006/045119 A2 | 4/2006 |
| WO | WO 2009/077907 A2 | 6/2009 |

OTHER PUBLICATIONS

U.S. Office Action dated Oct. 2, 2008 issued in U.S. Appl. No. 10/817,334.
U.S. Office Action dated Dec. 17, 2010 issued in U.S. Appl. No. 12/396,391.
U.S. Final Office Action dated Aug. 30, 2011 issued in U.S. Appl. No. 12/396,391.
U.S. Notice of Allowance dated Aug. 27, 2012 issued in U.S. Appl. No. 12/396,391.
Canadian Office Action Dated Apr. 13, 2012, issued in related Canadian Application No. 2,584,324.
European Supplementary Search Report dated Mar. 26, 2009 issued in EP 05 73 2924.5.
European Examination Report dated Jan. 24, 2011 issued in EP 05 73 2924.5-114.
European Examination Report dated Dec. 22, 2011 issued in EP 05 732 924.5.
Japanese Office Action (Notice of Reasons for Rejection) dated Jan. 13, 2011 issued in JP 2007-504067.
Translation of notice of Reasons for Rejection issued Jan. 12, 2011, for Japanese Application No. 2007-538151, 8 pgs.
"What is Blood Pressure?" (2002) [downloaded from http://web.archive.org/web/20020402233701/http://www.lifeclinic.com/focus/blood/whatisit.asp on Jan. 24, 2011] 2 pages.
American Diabetes Association, Position Statement—Diabetic Nephropathy (Jan. 2002), *Diabetes Care*, 25(1):585-589.
American Heart Association (2007), p. 1 and pp. 1-2 [http://www.americanheart.org/print_presenter.jhtml?idenfitier=2112].
AN 2000: 473143, CAPLUS abstract of Jefferson et al., "Solid-phase synthesis of a heterocyclic ethylenediamine-derivatized library," *J. Comb. Chem.*, 2(5):441-444 (2000) [abstract only].
Arand, M. et al., "Sequence similarity of mammalian epoxide hydrolases to the bacterial haloalkane dehalogenase and other related proteins" *FEBS Lett.*, 338:251-256 (1994).

Argiriadi, M.A. et al., "Binding of alkylurea inhibitors to epoxide hydrolase implicates active site tyrosines in substrate activation" J. Biol. Chem., 275:15265-15270 (2000).

Argiriadi, M.A. et al., "Detoxification of encirnomental mutagens and carcinogens: structure, A65 mechanism, and evolution of liver epoxide hydrolase" Proc. Natl. Acad. Sci. USA, 96:10637-10642 (1999).

Bardin, C. W. (ed.), Current Therapy in Endocrinology and Metabolism, 6th Edition, Mosby—Year Book, Inc., St. Louis, MO 1997.

Beetham, J. et al., "cDNA cloning and expression of a soluble epoxide hydrolase from human liver" Arch. Biochem. Biophys., 305(1):197-201 (1993).

Beetham, J. et al., "Gene evolution of epoxide hydrolases and recommended nomenclature" DNA Cell Biol., 14(1):61-71 (1995).

Campbell, W.B., "New role for epoxyeicosatrienoic acids as anti-inflammatory mediators" Trends Pharmacol. Sci., 21:125-127 (2000).

Capdevila, J.H. et al., "Cytochrome P450 and arachidonic acid bioactivation: molecular and functional properties of the arachidonate monooxygenase" J. Lipid. Res., 41:163-181 (2000).

Carroll, M.A. et al., "A new class of lipid mediators: cytochrome P450 arachidonate metabolites" Thorax, 55:S13-16 (2000).

CAS Accession No. 71: 18417; accessed 1212112006.

Chiasson, J. et al., "The efficacy of acarbose in the treatment of patients with non-insulin-dependent diabetes mellitus" Ann. Intern. Med., 121:928-935 (1994).

Chobanian et al., (2003) "Seventh Report of the Joint National Committee on Prevention, Detection, Evaluation, and Treatment of High Blood Pressure", JNC7—Complete Version, Hypertension 42:1206-1252, [downloaded from hyper.ahajournals.org on Jan. 28, 2011].

Coniff, R. et al., "Multicenter, placebo-controlled trial comparing acarbose (BAY g5421) with placebo, tolbutamide, and tolbutamide-plus-acarbose in non-insulin-dependent diabetes mellitus" Am. J. Med., 98:443-451 (1995).

Coniff, R. et al., "Acarbose: a review of US clinical experience" Clin. Ther., 19:16-26 (1997).

Davis et al. "Inhibitors of soluble epoxide hydrolase attenuate vascular smooth muscle cell proliferation," Proceedings of the National Academy of Sciences 99(4): 2222-2227 (Feb. 19, 2002).

Defronzo, R. et al. (eds.), "Introduction" Diabetes Reviews, 5(4):293 (1997).

Dudda, A. et al., "Lipid oxidation products in ischemic porcine heart tissue" Chem. Phys. Lipids, 82:39-51 (1996).

Epstein et al., (1992) "Diabetes mellitus and hypertension", Hypertension, 19(5):403-418, [downloaded from hyper.ahajournals.org on Jan. 28, 2011].

Fang et al., (2001), "Pathways of Epoxyeicosatrienoic Acid Metabolism in Endothelial Cells", J. Biol. Chem. 276:14867-14874.

Fang, X., et al., "Effect of soluble epoxide hydrolase inhibition on epoxyeicosatrienoic acid metabolism in human blood vessels" Am. J. Physiol. Heart Circ. Physiol. 287: H2412-H2420 (2004).

Fisslthaler, B. et al., "Cytochrome P450 2C is an EDHF synthase in coronary arteries" Nature, 401:493-497 (1999).

Fretland, A.J. et al., "Epoxide hyrolases: biochemistry and molecular biology" Chem. Biol. Intereract., 129:41-59 (2000).

Fukushima, A. et al., "Cardiovascular effects of leukotoxin (9, 10-epoxy-12-octadecenoate) and free fatty acids in dogs" Cardiovasc. Res., 22:213-218 (1988).

Gibson, G. G. and Skett, P., Introduction to Drug Metabolism, Second Ed., Chapman and Hall, New York pp. 199-210 (1994).

Grant, D. et al., "Molecular cloning and expression of murine liver soluble epoxide hydrolase" J. Biol.Chem., 268(23):17628-17633 (1993).

Haffner, S., "Management of dyslipidemia in adults with diabetes" Diabetes Care, 21:160-178 (1998).

Hammock, B.D. et al., "Chapter 3.18: Epoxide Hyrolases" in Comprehensive Toxicology. Oxford: Pergamon Press pp. 283-305 (1977).

Honig and Ingram, "Chronic Bronchitis, Emphysema, and Airways Obstruction" in Harrison's Principles of Internal Medicine, (Fauci et al., Eds.), 14th Ed., McGraw-Hill, New York, pp. 1451-1460(1998).

Huang et al, (2007) "Increasing or Stabilizing Renal Epoxyeicosatrienoic Acid Production Attenuates Abnormal Renal Function and Hypertension in Obese Rats", Am J Physiol Renal Physiol 293: F342-F349, [download from ajprenal.physiology.org on Nov. 24, 2010].

Hwang et al. "Orally Bioavailable Potent Soluble Epoxide Hydrolase Inhibitors" J. Medicinal Chemistry, 50(16): 3825-40 (2007).

Imig et al., (Oct. 2005) "An Orally Active Epoxide Hydrolase Inhibitor Lowers Blood Pressure and Provides Renal Protection in Salt-Sensitive Hypertension", NIH Public Access Author Manuscript, Hypertension; 46(4): 975-981 (15 pages).

Ishizaki, T. et al., "Endothelin-1 potentiates leukotoxin-induced edematous lung injury" J. Appl. Physiol., 79:1106-1611 (1995).

Ishizaki, T. et al., "Leukotoxin, 9, 10-epoxy-12-octadecenoate causes edematous lung injury via activation of vascular nitric oxide synthase" Am. J. Physiol., 269: L65-70 (1995).

Ishizaki, T. et al., "Leukotoxin, 9, 10-epoxy-12-octadecenoate causes pulmonary vasodilation in rats" Am. J. Physiol., 268: L123-128 (1995).

Iwamoto, Y. et al., "Effect of combination therapy of troglitazone and sulphonylureas in patients with type 2 diabetes who were poorly controlled by sulphonylurea therapy alone" Diabet. Med., 13:365-370 (1996).

Jefferson et al. "Solid-Phase Synthesis of a Heterocyclic Ethylenediamine-derivatized Library" J. Comb. Chem.2(5): 441-444 (2000) [Abstract Only].

Jung et al., (Aug. 2010) "Inhibition of the Soluble Epoxide Hydrolase Promotes Albuminuria in Mice with Progressive Renal Disease", Plos One, www.plosone.org, 5(8):1-10.

Kim, et al., "Design, synthesis, and biological activity of 1, 3-disubstituted ureas as potent inhibitors of the soluble epoxide hydrolase of increased water solubility" J. Med. Chem., 47:2110-2122 (2004).

Kricheldorf, H.R., et al., "Polykondensation von N-Aryloxycarbonyl-w-aminocarbonsauren and NPhenoxycarboyldipeptiden" Die Angewandte Mackromolekulare Chemie, 45(667):119-137 (1975).

Kwiterovich, P., "State-of-the-art update and review: clinical trials of lipid-lowering agents" Am. J. Cardiol., 82(12A):3U-17U (1998).

Lauterbach et al., (2002) "Cytochrome P450-Dependent Eicosapentaenoic Acid Metabolites are Novel BK Channel Activators", Hypertension, 39:609-613.

Lin et al. "Effect of 14, 15-epoxyeicosatrienoic acid infusion on blood pressure in normal and hypertensive rats," Biochemical and Biophysical Research Communications 167(3): 977-981 (Mar. 30, 1990).

Mahler, R. et al., "Type 2 diabetes mellitus: update on diagnosis, pathophysiology, and treatment" J. Clin. Endocrinol. Metab., 84:1165-71 (1999).

Manhiani, Marlina et al., (2009) "Soluble epoxide hydrolase gene deletion attenuates renal injury and inflammation with DOCA-salt hypertension", Am J Physiol Renal Physiol 297: F740-F748, [Downloaded from ajprenal.physiology.org on Nov. 23, 2010].

McElroy, N.R, et al., "QSAR and classification of murine and human soluble epoxide hydrolase inhibition by urea-like compounds" J. Med. Chem. 46:1066-1080 (2003).

Moghaddam, M.F. et al., "Bioactivation of leukotoxins to their toxic diols by epoxide hydrolase" Nat. Med., 3:562-567 (1997).

Morisseau, C., et al., "Inhibition of microsomal epoxide hydrolases by ureas, amides, and amines" Chem. Res. Toxicol. 14:409-415 (2001).

Morisseau, C., et al., "Potent urea and carbamate inhibitors of soluble epoxide hydrolases" Proc. Natl. Acad. Sci. USA, 96:8849-8854 (1999).

Morisseau, et al., "Structural refinement of inhibitors of urea-based soluble epoxide hydrolases" Biochem. Pharm., 63:1599-1608 (2002).

Nakagawa, Y., et al., "3-D QSAR analysis of inhibition of murine soluble epoxide hydrolase (MsEH) by benzoylureas, arylureas, and their analogues" Bioorg. Med. Chem. 8:2663-2673 (2000).

Newman, J.W. et al., "Evaluation of fish models of soluble epoxide hydrolase inhibition" Environ. Health Perspect., 109:61-66 (2001).

Node, K. et al., "Anti-inflammatory properties of cytochrome P450 epoxygenasederived eicosanoids" Science, 285:1276-1279 (1999).

Oesch, F. et al., "Mammalian epoxide hydrases: inducible enzymes catalyzing the inactivation of carcinogenic and cytotoxic metabolites derived from aromatic and olefinic compounds" *Xenobiotica*, 3:305-340 (1973).

Olearczyk, Jeffrey J. et al., (Jan. 2009) "Administration of a Substituted Adamantly-urea Inhibitor of Soluble Epoxide Hydrolase Protects the Kidney from Damage in Hypertensive Goto-Kakizaki Rats", *Clin Sci* (Lond); 116(1): 61-70, doi:10.1042/CS20080039.

Oltman, C.L. et al., "Epoxyeicosatrienoic acids and dihydroxyeicosatrienoic acids are potent vasodilators in the canine coronary microcirculation" *Circ Res.*, 83:932-939 (1998).

Osterby et al., (Apr. 2002) "Structural Changes in Renal Arterioles in Type I Diabetic Patients", , *Diabetogia*, 45(4) [Retrieved at http://www.ncbi.nih.nlm.hih.gov/entrez/query.fcgi?cmd=Retrieve&db=PubMed&list_uids=12. on May 30, 2007] 2 pages.

Ozawa, T. et al., "Existence of leukotoxin 9, 10-epoxy-12-octadecenoate in lung lavages from rats breathing pure oxygen and from patients with the adult respiratory distress syndrome" *Am. Rev. Respir. Dis.*, 137:535-540 (1988).

Reynolds, H.Y., "Interstitial lung diseases" in *Harrison's Principles of Internal Medicine*, (Fauci et al., Eds.), 14th Ed., McGraw-Hill, New York, pp. 1460-1466 (1998).

Sakai, T. et al., "Leukotoxin, 9,10-epoxy-12-octadecenoate inhibits mitochondrial respiration of isolated perfused rat lung" *Am. J. Physiol.*, 269:L326-331 (1995).

Severson et al. "Urea and amide-based inhibitors of the juvenile hormone epoxide hyrolase of the tobacco hornworm (Manduca sexta: Sphingidae)," *Insect Biochemistry and Molecular Biology* 32(12), pp. 1741-1756 (Dec. 2002).

Shankar et al., (Oct.-Dec. 2003) "Metabolic Syndrome: Its Pathogenesis and Management", *Journal, Indian Academy of Clinical Medicine*, 4(4):275-281.

Sinal, C.J. et al., "Targeted disruption of soluble epoxide hydrolase reveals a role in blood pressure regulation" *J. Biol. Chem.*, 275:40504-405010 (2000).

Speizer, "Environmental Lung Diseases," *Harrison's Principles of Internal Medicine*, (Fauci et al., Eds.), 14th Ed., 1998, McGraw-Hill, New York, pp. 1429-1436.

Turner, N. et al., "Insulin resistance, impaired glucose tolerance and non-insulin-dependent diabetes, pathologic mechanisms and treatment: Current status and therapeutics possibilities" *Prog. Drug Res.*, 51:33-94 (1998).

United Kingdom Prospective Diabetes Study Group, "UKPDS 28: a randomized trial of efficacy of early addition of metformin in sulfonylurea-treated type 2 diabetes", *Diabetes Care*, 21: 87-92 D (1998).

Walter, E. et al., "Transepithelial transport properties of peptidomimetic thrombin inhibitors in monolayers of a human intestinal cell line (Caco-2) and their correlation to in vivo data" *Pharm. Res.*, 12: D 360-365 (1995).

Watanabe, K. et al., "Studies on intestinal absorption of sulpiride (2): transepithelial transport of sulpiride across the human intestinal cell line caco-2" *Biol. Pharm. Bull.*, 25:1345-1350 (2002).

Watanabe, T., et al., "In vitro metabolism of the mammalian soluble epoxide hydrolase inhibitor, 1-cyclohexyl-3-dodecyl-urea" *Drug Metab. Dispos.* 31 (7):846-853 (2003).

Watanabe, T., et al., "Rapid Determination of Soluble Epoxide Hydrolase Inhibitors in Rat Hepatic Microsomes by High-Perfonmance Liquid Chromatography With Electrospray Tandem Mass D Spectrometry," *Analytical Biochemistry*, 299(2):227-234, (2001).

Weintraub, N.L. et al., "Epoxide hydrolases regulate epoxyeicosatrienoic acid incorporation into coronary endothelial phospholipids" *Am. J. Physiol.*, 277:H2098-2108 (1992).

White, RW, et al., "Aliphatic hydroxylation by cytochrome P-450. Evidence for rapid hydrolysis of an intermediate iron-nitrene complex," *J. Am. Chem.*, vol. 1 06(17), pp. 4922-4926 (1984).

Yamada, T., et al., "Biochemical Evidence for the Involvement of Tyrosine in Epoxide Activation During the Catalytic Cycle of Epoxide Hydrolase," *J. Biol. Chem.*, 275(39): 23082-20388 (Jul. 28, 2000).

Yu, Z. et al., "Soluble epoxide hydrolase regulates hydrolysis of vasoactive epoxyeicosatrienoic acids" *D Circ. Res.*, 87:992-998 (2000).

Zeldin, D.C., et al., "Regie- and enantiofacial selectivity of epoxyeicosatrienoic acid hydration by D cytosolic epoxide hydrolase" *J. Biol. Chem.*, 268:6402-6407 (1993).

Zhao, X., et al., "Soluble epoxide hydrolase inhibition protects the kidney from hypertension-induced damage" *J. Am. Soc. Nephrol.* 15:1244-1253 (2004).

Zhao, Xueying et al. (2004) "Soluble Epoxide Hydrolase Inhibition Protects the Kidney from Hypertension-Induced Damage", *J Am Soc Nephrol* 15: 1244-1253.

Zheng, J. et al.,"Leukotoxin-Dial: a putative toxic mediator involved in acute respiratory distress D syndrome" *Am. J. Respir. Cell Mol. Biol.*, 25:434-438 (2001).

U.S. Notice of Allowance dated Feb. 11, 2013 issued in U.S. Appl. No. 12/396,391.

\* cited by examiner

REDUCING NEPHROPATHY WITH INHIBITORS OF SOLUBLE EPOXIDE HYDROLASE AND EPOXYEICOSANOIDS

CROSS-REFERENCES TO RELATED APPLICATIONS

This application is a continuation of U.S. application Ser. No. 11/719,092, filed May 10, 2007, which is a national stage filing under 35 U.S.C. 371 of International Application PCT/US2005/008765, filed on Mar. 16, 2005, which claims the benefit of U.S. Provisional Application No. 60/553,847, filed Mar. 16, 2004. This application is also a continuation-in-part of U.S. application Ser. No. 12/396,391, filed on Mar. 2, 2009, which is a continuation of U.S. application Ser. No. 10/817,334, filed on Apr. 2, 2004, which claims the benefit of U.S. Provisional Application No. 60/460,559, filed on Apr. 3, 2003. The contents of which each of these applications are hereby incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with Government support under Grant Nos. DK35747 and ES02710 awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

In 2003, the International Diabetes Federation estimated that there were 194 million people worldwide with diabetes. Of these, some 16 million were estimated to be in the United States. Many diabetes sufferers undergo a slow deterioration of the kidneys, a process known as nephropathy. The end stage of nephropathy is kidney failure, or end stage renal disease. Nephropathy and kidney failure can result even when diabetes is controlled with drugs and exercise. According to the National Institute of Diabetes and Digestive and Kidney Diseases (NIDDK) of the National Institutes of Health, diabetes is the most common cause of kidney failure and is responsible for about 40% of the 100,000 cases of kidney failure that develop annually in the U.S. Given the $20 billion annual cost of treating kidney failure in the U.S. alone, reducing nephropathy and kidney failure could significantly reduce the costs of treating this complication of diabetes.

The NIDDK website on diabetes states that, over several years, people with diabetes who are developing kidney disease will have small amounts of the blood protein albumin begin to leak into their urine. At its first stage, this condition is called microalbuminuria. The kidney's filtration function usually remains normal during this period. As the disease progresses, more albumin leaks into the urine. Various names are attached to this interval of the disease, such as overt diabetic nephropathy or macroalbuminuria. As the amount of albumin in the urine increases, filtering function usually begins to drop. The body retains various wastes as filtration falls. Creatinine is one such waste, and a blood test for creatinine can measure the decline in kidney filtration. There are multiple hypotheses about the presence of protein in the urine. One hypothesis is that the protein is an indication of the degree of renal failure. Another is that the leakage of protein from the kidney is not just a symptom of renal failure, but actively contributes to it.

Hypertension is considered a significant factor in the development of nephropathy, and kidney damage tends to increase hypertension. Both a family history of hypertension and the presence of hypertension appear to increase chances of developing kidney disease. Hypertension also accelerates the progress of kidney disease where it already exists. The American Diabetes Association and the National Heart, Lung, and Blood Institute recommend that people with diabetes keep their blood pressure below 130/80. Many people require two or more drugs to control their blood pressure.

Renin, an enzyme released by the kidney, cleaves a circulating substrate known as angiotensinogen. Angiotensinogen is cleaved by renin to form a decapeptide, angiotensin I. Angiotensin I is cleaved by angiotensin-converting enzyme (ACE) to form the octapeptide angiotensin II. Angiotensin II binds to receptors, which results in a number of biological effects, one of which is to cause blood vessels to constrict, increasing blood pressure.

Administration of inhibitors of ACE or of angiotensin receptor blocker (ARB) therefore helps reduce hypertension. Beta blockers, calcium channel blockers, and other blood pressure drugs may also be needed.

Hypertension alone, however, cannot explain nephropathy due to diabetes, since bringing blood pressure down to normal levels will slow development of nephropathy, but will not block it. Progress has been made in slowing the onset and progression of kidney disease in people with diabetes. The NIDDK website on diabetes indicates that drugs used to lower blood pressure can slow the progression of kidney disease significantly, and that both ACE inhibitors and ARBs have proven effective in slowing the progression of kidney disease. One hypothesis is that damage to the glomeruli causes changes to the microcirculation that causes increased sensitivity to angiotensin II.

An example of an effective ACE inhibitor is captopril, which doctors commonly prescribe for treating kidney disease or diabetes. In addition to its ability to lower blood pressure, captopril may directly protect the kidney's glomeruli. ACE inhibitors have lowered proteinuria and slowed deterioration even in diabetic patients who did not have high blood pressure. Further, in persons with type 1 diabetes, ACE inhibitors have been shown to reduce the progression of kidney damage more than other agents that reduce blood pressure by an equal degree. An example of an effective ARB is losartan, which has also been shown to protect kidney function and lower the risk of cardiovascular events.

Methods of determining whether an agent protects against diabetic nephropathy are known in the art, and typically involve determining whether persons administered a putative protective agent release less protein into their urine than persons administered a placebo. See, e.g., Lewis et al. "The effect of angiotensin-converting-enzyme inhibition on diabetic nephropathy The Collaborative Study Group" N Engl J Med 329(20):1456-1462 (1993); Ruggenenti et al., "Chronic proteinuric nephropathies: outcomes and response to treatment in a prospective cohort of 352 patients with different patterns of renal injury," Am J Kidney Dis. 35(6):1155-1165 (2000); Maschio et al., "Effect of the angiotensin-converting-enzyme inhibitor benazepril on the progression of chronic renal insufficiency. The Angiotensin-Converting-Enzyme Inhibition in Progressive Renal Insufficiency Study Group." N Engl J Med. 334(15):939-945 (1996); and Hannedouche et al. "Angiotensin converting enzyme inhibition and chronic cyclosporine-induced renal dysfunction in type 1 diabetes," Nephrol Dial Transplant. 11(4):673-678 (1996).

Additional means of slowing or blocking development of nephropathy are needed. It would be useful to find additional agents or types of agents that can protect the kidney from damage.

Epoxide hydrolases ("EH," EC 3.3.2.3) are a family of enzymes which hydrolyze a variety of exogenous and endogenous epoxides to their corresponding diols. Epoxide hydrolases have been found in tissues of all mammalian species tested. The highest levels of the enzyme were found in liver and kidney cells (see Wixtrom and Hammock, Pharmacology and Toxicology (Zakim, D. and Vessey, D. A., ed.) 1:1-93, Wiley, New York, 1985).

Four principal EH's are known: leukotriene epoxide hydrolase, cholesterol epoxide hydrolase, microsomal EH ("mEH"), and soluble EH ("sEH," previously called cytosolic EH). The leukotriene EH acts on leukotriene $A_4$, whereas the cholesterol EH hydrates compounds related to the 5,6-epoxide of cholesterol (Nashed, N. T., et al., Arch. Biochem. Biophysics., 241:149-162, 1985; Finley, B. and B. D. Hammock, Biochem. Pharmacol., 37:3169-3175, 1988).

The microsomal epoxide hydrolase metabolizes monosubstituted, 1,1-disubstituted, cis-1,2-disubstituted epoxides and epoxides on cyclic systems epoxides to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance.

Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. For instance, cytochrome P450 epoxygenase catalyzes NADPH-dependent enatioselective epoxidation of arachidonic acid to four optically active cis-epoxyeicosantrienoic acids ("EETs") (Karara, A., et al., J. Biol. Chem., 264:19822-19877, (1989)). Soluble epoxide hydrolase has been shown in vivo to convert these compounds with regio- and enantiofacial specificity to the corresponding vic-dihydroxyeicosatrienoic acids ("DHETs"). Both liver and lung cytosolic fraction hydrolyzed 14,15-EET, 8,9-EET and 11,12-EET, in that order of preference. The 5,6 EET is hydrolyzed more slowly. Purified sEH selected 8S,9R- and 14R,15S-EET over their enantiomers as substrates. Studies have revealed that EETs and their corresponding DHETs exhibit a wide range of biological activities. Some of these activities include involvements in luteinizing hormone-releasing hormone, stimulation of luteinizing hormone release, inhibition of $Na^+/K^+$ ATPase, vasodilation of coronary artery, mobilization of $Ca^{2+}$ and inhibition of platelet aggregation. Soluble epoxide hydrolase is believed to play a role in these biological activities by contributing to the regulation of the steady state levels of EETs and DHETs as well as other biologically active epoxides and diols.

BRIEF SUMMARY OF THE INVENTION

The present invention provides uses, methods, and compositions. In one group of embodiments, the invention provides uses of an inhibitor of soluble epoxide hydrolase ("sEH") for the manufacture of a medicament for inhibiting development or progression of nephropathy in (a) a person with diabetes mellitus whose blood pressure is 130/80 or less, (b) a person with metabolic syndrome whose blood pressure is less than 130/85, (c) a person with a triglyceride level over 215 mg/dL, or (d) a person with a cholesterol level over 200 mg/dL. In some embodiments, the inhibitor of sEH is selected from the group consisting of an isomer of adamantyl dodecyl urea, N-cyclohexyl-N'-dodecyl urea (CDU) and N,N'-dicyclohexylurea (DCU). The medicament can be a slow release formulation. Optionally, the medicament further comprises a cis-epoxyeicosantrienoic acid ("EET"). The EET can be, for example, 14,15-EET, 8,9-EET or 11,12-EET, and in some uses can be 14R,15S-EET. In some embodiments, the person has Type 2 diabetes, or has Type 1 diabetes. In some embodiments, the person has metabolic syndrome. In some embodiments, the person has a triglyceride level over 215 mg/dL. In some embodiments, the person has a cholesterol level over 200 mg/dL.

In a further group of embodiments, the invention provides uses of a nucleic acid that inhibits expression of soluble epoxide hydrolase ("sEH") for the manufacture of a medicament for inhibiting development or progression of nephropathy in (a) a person with diabetes mellitus whose blood pressure is 130/80 or less, (b) a person with metabolic syndrome whose blood pressure is less than 130/85, (c) a person with a triglyceride level over 215 mg/dL, or (d) a person with a cholesterol level over 200 mg/dL. In some embodiments, the nucleic acid is a small interfering RNA ("siRNA").

In yet a further group of embodiments, the invention provides for the use of a cis-epoxyeicosantrienoic acid ("EET") for the manufacture of a medicament to treat hypertension. In some embodiments, the EET is 14,15-EET, 8,9-EET, or 11,12-EET. In some embodiments, the EET is 14R,15S-EET. In some embodiments, the EET is in a material which releases the EET into the surrounding environment over time.

In still another group of embodiments, the invention provides methods of inhibiting progression of nephropathy in a person with diabetes mellitus whose blood pressure is 130/80 or less, a person with metabolic syndrome whose blood pressure is less than 130/85, a person with a triglyceride level over 215 mg/dL, and a person with a cholesterol level over 200 mg/dL, comprising administering an inhibitor of soluble epoxide hydrolase ("sEH") to the person. In some embodiments, the inhibitor of sEH is selected from the group consisting of an isomer of adamantyl dodecyl urea, N-cyclohexyl-N'-dodecyl urea (CDU) and N,N'-dicyclohexylurea (DCU). In some embodiments, the person has Type 2 diabetes. In some embodiments, the person has Type 1 diabetes. In some embodiments, the person has metabolic syndrome. In some embodiments, the person has a triglyceride level over 215 mg/dL. In some embodiments, the person has a cholesterol level over 200 mg/dL. In some embodiments, the inhibitor of sEH is in a material which releases the inhibitor over time. In some embodiments, the method further comprises administering a cis-epoxyeicosantrienoic acid ("EET"). In some embodiments, the EET is selected from the group consisting of 14,15-EET, 8,9-EET and 11,12-EET. The EET can be 14R,15S-EET. In some embodiments, the EET is in a material which releases the EET into its surroundings over time. In some embodiments, the inhibitor is administered orally. The inhibitor can be administered in a total daily dose from about 0.001 µM/kg to about 100 mg/kg body weight of the patient.

In another group of embodiments, the invention provides methods of inhibiting progression of nephropathy in (a) a person with diabetes mellitus whose blood pressure is 130/80 or less, (b) a person with metabolic syndrome whose blood pressure is less than 130/85, (c) a person with a triglyceride level over 215 mg/dL, or (d) a person with a cholesterol level over 200 mg/dL, the method comprising administering to said patient a nucleic acid which inhibits expression of a gene encoding soluble epoxide hydrolase. In some embodiments, the nucleic acid is a small interfering RNA ("siRNA").

In yet another group of embodiments, the invention provides methods of reducing blood pressure in a person in need thereof. The method comprises administering to the person an inhibitor of soluble epoxide hydrolase and a cis-epoxyeicosantrienoic acid ("BET"). In some embodiments, the EET is selected from the group consisting of 14,15-EET, 8,9-EET and 11,12-EET. In some embodiments, the EET is 14R,15S-EET. The EET can be in a material which releases the EET into the surroundings over time.

The invention further provides compositions comprising a cis-epoxyeicosantrienoic acid ("EET") coated with a material insoluble in an acid of pH 3 but soluble in a solution with a pH of 7.4 or higher. The EET can be 14,15-BET, 8,9-EET or 11,12-EET, and can preferably be 14R,15S-EET.

BRIEF DESCRIPTION OF THE DRAWINGS

Not applicable.

DETAILED DESCRIPTION OF THE INVENTION

I. Introduction

A. sEH Inhibitors and EETs Inhibit Development of Nephropathy

It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure, including those who suffer from diabetes.

Surprisingly, it has now been discovered that, in addition to their effect in reducing hypertension, sEH inhibitors can reduce damage to the kidney, and especially damage to kidneys from diabetes, as measured by albuminuria. Like angiotensin-converting enzyme (ACE) inhibitors, sEH inhibitors can reduce kidney deterioration (nephropathy) from diabetes even in individuals who do not have high blood pressure. Although sEH inhibitors have been previously found to reduce hypertension and to inhibit inflammation, there are numerous agents that reduce hypertension or that reduce inflammation that have no known or apparent effect on kidney damage. Thus, there was no reason to expect that sEH inhibitors would have an effect on kidney damage. Since sEH inhibitors are not part of the renin-angiotensin system modulated by ACE inhibitors and ARB inhibitors, there was no reason to expect that sEH inhibitors would have a protective effect on kidney function over their anti-hypertensive and anti-inflammatory effects.

It has also now been discovered that cis-epoxyeicosantrienoic acids ("EETs") can be used in conjunction with sEH inhibitors to further reduce kidney damage. EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease.

EETs are well known in the art. EETs useful in the methods of the present invention include 14,15-BET, 8,9-EET and 11,12-BET, and 5,6 EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-BET, and 14R,15S-EET, are commercially available from, for example, Sigma-Aldrich (catalog nos. E5516, E5641, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

EETs have not previously been administered therapeutically, largely because it has been believed they would be hydrolyzed too quickly by endogenous sEH to be helpful. It was not known whether endogenous sEH could be inhibited sufficiently to raise EET levels over those normally present. Surprisingly, it is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs can be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In preferred embodiments, the EETs, the sEH inhibitor, or both, are provided in a material that permits them to be released over time to provide a longer duration of action. Slow release coatings are well known in the pharmaceutical art; the choice of the particular slow release coating is not critical to the practice of the present invention.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially. Such enteric coatings may be used to protect EETs during passage through the stomach. A exemplar coating is set forth in the Examples.

While the anti-hypertensive effects of EETs have been recognized, EETs have not been administered to treat hypertension because it was thought endogenous sEH would hydrolyse the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors has reduced the endogenous concentrations of EETs below those normally present in healthy individuals. Administration of exogenous EETs in conjunction with an sEH inhibitor is therefore expected to be beneficial and to augment the effects of the sEH inhibitor in reducing the progression of diabetic nephropathy.

B. Renal Damage and Diabetes

Diabetes mellitus (generally referred to herein as "diabetes") is a heterogeneous group of metabolic disorders, connected by raised plasma glucose concentration and disturbance of glucose metabolism. It is a chronic condition characterized by the presence of fasting hyperglycemia and the development of widespread premature atherosclerosis. The hyperglycemia in diabetes mellitus generally results from defects in insulin secretion, insulin action, or both. The World Health Organization (WHO) has set forth a classification scheme for diabetes mellitus that includes type 1 diabetes mellitus, type 2 diabetes mellitus, gestational diabetes, and other specific types of diabetes mellitus. These terms have largely displaced the formerly used terms IDDM (insulin-dependent diabetes mellitus), NIDDM (non-insulin dependent diabetes mellitus), juvenile-onset diabetes mellitus and adult-onset diabetes mellitus.

Type 1 diabetes results from an autoimmune destruction of the insulin-secreting B-cells of the pancreas. There are several markers of this autoimmune destruction, detectable in body fluids and tissues, including islet cell autoantibodies, autoantibodies to insulin, autoantibodies to glutamic acid decarboxylase (GAD65), and autoantibodies to the tyrosine phosphatases IA-2 and IA-2B. While genetic factors are strongly implicated, the concordance rate in twin studies is under 50% and supports a role for environmental factors, which are said to include viral infections. The autoimmune process typically begins many years before clinical detection and presentation. The rate of B-cell destruction is quite variable, being rapid in some individuals (mainly infants and children) and usually slow in adults.

Type 2 diabetes disease usually develops after 40 years of age. It is much more common that type 1 diabetes and comprises approximately 90% of all individuals with diabetes. Insulin concentrations are mostly increased but they can be normal or decreased. Obesity is common. Diet and exercise regimens leading to weight reduction can ameliorate hyperglycemia. Oral hypoglycaemic drugs are also used in an effort to lower blood sugar. Nevertheless, insulin is sometimes required to correct hyperglycemia, particularly as patients grow older or as their β-cells fail.

Two groups of disorders may be said to typify type 2 diabetes mellitus. The first one is a decreased ability of insulin to act on peripheral tissues, usually referred to as "insulin resistance." Insulin resistance is defined as a decreased biological response to normal concentrations of circulating insulin and represents the primary underlying pathological process. The second is the dysfunction of pancreatic B-cells, represented by the inability to produce sufficient amounts of insulin to overcome insulin resistance in the peripheral tissues. Eventually, insulin production can be insufficient to compensate for the insulin resistance due to B-cell dysfunction. The common result is a relative deficiency of insulin. Data support the concept that insulin resistance is the primary defect, preceding the derangement of insulin secretion. As with type 1 diabetes, the basis of the insulin resistance and insulin secretion defects is believed to be a combination of environmental and genetic factors.

Type 1 and Type 2 diabetes comprise the great majority of cases of diabetes. In addition to these, there is gestational diabetes, which is usually asymptomatic, and a heterogeneous collection of specific types of diabetes resulting from pathologies of the pancreas, pathologies of the endocrine system, infection, or exposure to chemicals or drugs which damage the beta cells of the pancreas. The present invention can be used with regard to any form of diabetes to the extent that it is associated with progressive damage to the kidney or kidney function. While persons with diabetes caused by autoimmune processes, such as in Type 1 diabetes, will benefit from the administration of sEH inhibitor, with or without EETs, in preferred embodiments relating to diabetes, the invention relates to persons whose diabetes is not caused by an autoimmune process. Therefore, in some preferred embodiments, the person has Type 2 diabetes; in some preferred embodiments, the individual has one of the various types of diabetes caused by non-autoimmune processes described earlier in this paragraph.

The chronic hyperglycemia of diabetes is associated with long-term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

Glycation of tissue proteins and other macromolecules and excess production of polyol compounds from glucose are among the mechanisms thought to produce tissue damage from chronic hyperglycemia. The nonenzymatic glycation process in one in which glucose is chemically bound to amino groups of proteins, but without the help of enzymes. It is a covalent reaction where, by means of N-glycoside bonding, sugar-protein complex is formed through a series of chemical reactions described by Maillard. In Maillard reactions, sugar-reacts with protein to form complexes and represent an early product of nonenzymatic glycation and an intermediary that is a precursor of later compounds. Numerous intermediary products are then formed, followed by complex product polymerization reactions resulting in heterogeneous structures called advanced glycation endproducts (AGE). It has also been reported that AGEs progressively accumulate on the tissues and organs that develop chronic complications of diabetes mellitus like retinopathy, nephropathy, neuropathy and progressive atherosclerosis. Immunohistochemical methods have demonstrated the presence of different AGE compounds in glomeruli and tubuli cells in both experimental and human diabetic nephropathy. Glycation in diabetes and AGEs are discussed in, for example, U.S. Application Nos. 20030203973 and 20030092744 and U.S. Pat. Nos. 6,624,178 and 5,518,720.

In 2002, the American Diabetes Association published a position statement entitled "Diabetic Nephropathy," at Diabetes Care 25:S85-S89 (2002) (the "Statement"). According to the Statement, the "earliest clinical evidence of nephropathy is the appearance of low but abnormal levels (30 mg/day or 20 μg/min) of albumin in the urine, referred to as microalbuminuria." In persons with Type 1 diabetes (juvenile diabetes, characterized by an inability to produce sufficient insulin), the Statement states that 80% of persons with microalbuminuria will gradually progress to overt nephropathy, with hypertension developing along the way, unless specific interventions are introduced, although they may have hypertension that becomes manifest about the time they develop microalbuminuria. The Statement further indicates that a higher proportion of persons with Type 2 diabetes (adult-onset, characterized by a reduced ability to respond to insulin) have microalbuminuria at diagnosis, and that 20-40% will progress to overt nephropathy without specific intervention. The Statement indicates that one third of Type 2 patients have hypertension at diagnosis, thereby indicating that two thirds do not. This is particularly important since the number of people with type 2 diabetes is significantly larger than the number that develop type 1 diabetes.

C. Metabolic Syndrome and Dyslipidemia

An increasing number of American adults are considered to have metabolic syndrome. Metabolic syndrome, also known as "syndrome X" and "insulin resistance syndrome" affects 1 in 4 American adults, and the percentage increases with age. As defined on the Mayo Clinic website, metabolic syndrome is not a single disease, but a cluster of disorders of metabolism that are associated with increased risk of type 2 diabetes, stroke, and heart disease. Among these disorders are obesity, particularly around the abdomen, hypertension, high levels of triglycerides in the blood, and resistance to insulin. The more of the risk factors possessed by an individual, the more likely the individual is to develop type 2 diabetes, stroke, or heart disease. The National Cholesterol Education Program defines an individual as having metabolic syndrome if they have three or more of the following measurements: abdominal obesity, measured as a waist circumference of greater than 35 inches for women and 40 inches for men, triglyceride levels of 150 milligrams per deciliter (mg/dL) or higher, blood pressure of 130/85 millimeters of mercury or higher, a fasting blood sugar level of 110 mg/dL or higher, and a level of high-density lipoprotein cholesterol lower than 50 mg/dL for women and 40 mg/dL for men.

Persons with metabolic syndrome are therefore at high risk of progression to type 2 diabetes, and therefore at higher risk than average for diabetic nephropathy. It is therefore desirable to monitor such individuals for microalbuminuria, and to administer an sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some preferred embodiments, the person has metabolic syndrome and blood pressure below 130/85.

Another risk factor for heart disease is dyslipidemia, that is, disorders of lipoprotein metabolism. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. In the past, the dogma was that damage to the kidneys was due to high levels of cholesterol; it is now believed that high levels of triglycerides are also associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of the inhibitors, with or without the EETs, can reduce the need to administer statin drugs (HMG-CoA reductase inhibitors) to the patients, or reduce the amount of the statins needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/dL and blood pressure below 130/85

D. sEH Inhibitors and EETs

Scores of sEH inhibitors are known, of a variety of chemical structures. The sEH enzyme can be selectively and competitively inhibited in vitro by a variety of urea, carbamate, and amide derivatives (Morisseau et al., Proc. Natl. Acad. Sci. U.S.A, 96:8849-8854 (1999)). U.S. Pat. No. 5,955,496 (the '496 patent) sets forth a number of suitable epoxide hydrolase inhibitors for use in the methods of the invention. One category of inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods of the invention are set forth in U.S. Pat. Nos. 6,150,415 (the '415 patent) and 6,531,506 (the '506 patent), as well as in co-owned applications PCT/US2004/010298, published as WO 2004/089296 and U.S. application Ser. No. 10/817,334, published as U.S. Patent Application Publication 2005/0026844. The '506 patent, for example, shows several score of inhibitors of sEH of two types and the concentrations at which they were shown to inhibit 50% of sEH activity. Any particular inhibitor can readily be tested to determine whether it will work in the methods of the invention by standard assays, such as that set forth in the Examples, below.

Derivatives in which the urea, carbamate, or amide pharmacophore (as used herein, "pharmacophore" refers to the section of the structure of a ligand that binds to the sEH) is covalently bound to both an adamantane and to a 12 carbon chain dodecane are particularly useful as sEH inhibitors. Derivatives that are metabolically stable are preferred, as they are expected to have greater activity in vivo.

Derivatives of urea are transition state mimetics that form a preferred group of sEH inhibitors. Within this group, DCU is preferred as an inhibitor, while CDU is more preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH.) Thus, isomers of adamantyl dodecyl urea are particularly preferred inhibitors. It is further expected that N,N'-dodecyl-cyclohexyl urea (DCU), and other inhibitors of sEH, and particularly dodecanoic acid ester derivatives of urea, are suitable for use in the methods of the invention. Preferred inhibitors include:

12-(3-Adamantan-1-yl-ureido)dodecanoic acid (AUDA)

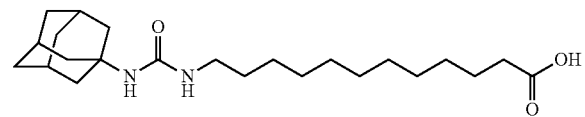 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE)

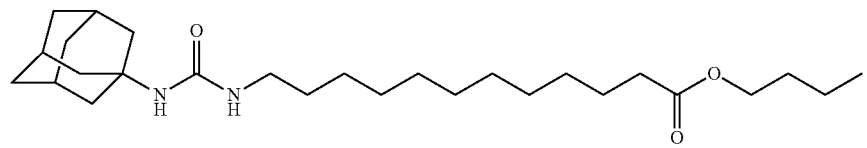 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950)

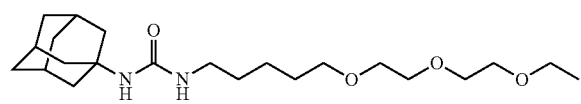 [SMILES: CCOCCOCCOCCCCCNC(=O)NC12CC3CC(CC(C3)C1)C2]

A number of other inhibitors, each of which is preferred for use in the methods and compositions of the invention, are set forth in co-owned applications PCT/US2004/010298 and U.S. Patent Application Publication 2005/0026844.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value. See, e.g., Thomas, G., Medicinal Chemistry: an introduction, John Wiley & Sons Ltd. (West Sussex, England, 2000)). Since the uses of the invention contemplate inhibition of sEH over periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly, including materials that release the inhibitor in or near the kidney, to provide a high local concentration. Methods of administration that permit high local concentrations of an inhibitor over a period of time are known, and are not limited to use with inhibitors which have short half lives although, for inhibitors with a relatively short half life, they are a preferred method of administration.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

II. Definitions

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases.

"Epoxide hydrolases" ("EH;" EC 3.3.2.3) are enzymes in the alpha beta hydrolase fold family that add water to 3 membered cyclic ethers termed epoxides.

"Soluble epoxide hydrolase" ("sEH") is an enzyme which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., DNA Cell Biol. 14(1): 61-71 (1995). Soluble epoxide hydrolase represents a single highly conserved gene product with over 90% homology between rodent and human (Arand et al., FEBS Lett., 338: 251-256 (1994)). Unless otherwise specified, as used herein, the terms "soluble epoxide hydrolase" and "sEH" refer to human sEH.

Unless otherwise specified, as used herein, the term "sEH inhibitor" refers to an inhibitor of human sEH. Preferably, the inhibitor does not also inhibit the activity of microsomal epoxide hydrolase by more than 25%, and more preferably does not inhibit it by more than 10%, at concentrations at which the inhibitor inhibits sEH by at least 50%.

The "nephron" is the primary unit for urine production and blood filtration in the kidney.

"Nephropathy" refers to any of several pathological conditions of the nephron. Diabetes causes a variety of pathologies associated with the kidney (See, e.g., Primer on Kidney Diseases, 3rd Edition, National Kidney Foundation, Arthur Greenberg ed., Academic Press, San Francisco, Calif., 2001)

By "physiological conditions" is meant an extracellular milieu having conditions (e.g., temperature, pH, and osmolarity) which allows for the sustenance or growth of a cell of interest.

III. Inhibitors of Epoxide Hydrolases

A number of inhibitors of epoxide hydrolases are known. In preferred embodiments, the epoxide hydrolase inhibited is soluble epoxide hydrolase, or "sEH." Preferably, the inhibitor inhibits sEH without also significantly inhibiting microsomal epoxide hydrolase ("mEH"). Preferably, at concentrations of 500 µM, the inhibitor inhibits sEH activity by at least 50% while not inhibiting mEH activity by more than 10%. Preferred compounds have an IC50 (inhibition potency or, by definition, the concentration of inhibitor which reduces enzyme activity by 50%) of less than about 500 µM. Inhibitors with IC50s of less than 500 µM are preferred, with IC50s of less than 100 µM being more preferred and IC50s of 50 µM, 40 µM, 30 µM, 25 µM, 20 µM, 15 µM, 10 µM, 5 µM, 3 µM, 2 µM, 1 µM or even less being the more preferred as the IC50 decreases. Assays for determining EH activity are known in the art and described elsewhere herein.

Two preferred classes of inhibitors of the invention are compounds of Formulas 1 and 2, as described in U.S. Pat. Nos. 6,150,415 and 6,531,506, incorporated herein by reference. Means for preparing such compounds and assaying desired compounds for the ability to inhibit epoxide hydrolases are also described. The '506 patent, in particular, teaches scores of inhibitors of Formula 1 and some twenty inhibitors of Formula 2, which were shown to inhibit human sEH at concentrations as low as 0.1 µM.

In addition to the compounds in Formula 1 which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an $\alpha/\beta$-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

IV. EETs

EETs can be administered to inhibit the development or worsening of nephropathy. In preferred embodiments, one or more EETs are administered concurrently or after administration of an sEH inhibitor so that the EET or EETs are not hydrolyzed quickly.

Optionally, the EET or EETs are embedded or otherwise placed in a material that releases the EET over time. Materials suitable for promoting the slow release of compositions such as EETs are known in the art.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". An exemplar coating of this type is set forth in the Examples. The choice of the particular enteric coating is not critical to the practice of the invention.

Preferred EETs include 14,15-EET, 8,9-EET and 11,12-EET in that order of preference. Purified sEH selected 8S,9R- and 14R,15S-EET; accordingly these EETs are particularly preferred. 8,9-EET, 11,12-EET, and 14R,15S-EET are commercially available from, for example, Sigma-Aldrich (catalog nos. E5516, E5641, and E5766, respectively, Sigma-Aldrich Corp., St. Louis, Mo.).

V. Assays for Epoxide Hydrolase Activity

Any of a number of standard assays for determining epoxide hydrolase activity can be used to determine inhibition of sEH. For example, suitable assays are described in Gill, et al., *Anal Biochem* 131, 273-282 (1983); and Borhan, et al., *Analytical Biochemistry* 231, 188-200 (1995)). Suitable in vitro assays are described in Zeldin et al., *J Biol. Chem.* 268:6402-6407 (1993). Suitable in vivo assays are described in Zeldin et al., *Arch Biochem Biophys* 330:87-96 (1996). Assays for epoxide hydrolase using both putative natural substrates and surrogate substrates have been reviewed (see, Hammock, et al. *In: Methods in Enzymology, Volume III, Steroids and Isoprenoids, Part B*, (Law, J. H. and H. C. Rilling, eds. 1985), Academic Press, Orlando, Fla., pp. 303-311 and Wixtrom et al., *In: Biochemical Pharmacology and Toxicology, Vol. 1: Methodological Aspects of Drug Metabolizing Enzymes*, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. *Anal. Biochem.* 174:291-299 (1985) and Dietze, et al. *Anal. Biochem.* 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

VI. Other Means of Inhibiting sEH Activity

Other means of inhibiting sEH activity or gene expression can also be used in the methods of the invention. For example, a nucleic acid molecule complementary to at least a portion of the human sEH gene can be used to inhibit sEH gene expression. Means for inhibiting gene expression using, for example, short interfering RNA (siRNA), are known. "RNA interference", a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo. In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories rushed to have siRNA made to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; nucleotides 42-1703 of SEQ ID NO:1 are the nucleic acid sequence encoding the amino acid sequence.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and nonprofit researchers, from the Whitehead Institute for Biomedical Research on the interne by entering "http://" followed by "jura.wi.mit.edu/pubint/http://iona.wi.mit.edu/siRNAext/." For example, using the program available from the Whitehead Institute, the following sEH target sequences and siRNA sequences can be generated:

1) Target: (SEQ ID NO: 3)
CAGTGTTCATTGGCCATGACTGG

Sense-siRNA: (SEQ ID NO: 4)
5'-GUGUUCAUUGGCCAUGACUTT-3'

Antisense-siRNA: (SEQ ID NO: 5)
5'-AGUCAUGGCCAAUGAACACTT-3'

2) Target: (SEQ ID NO: 6)
GAAAGGCTATGGAGAGTCATCTG

Sense-siRNA: (SEQ ID NO: 7)
5'-AAGGCUAUGGAGAGUCAUCTT-3'

Antisense-siRNA: (SEQ ID NO: 8)
5'-GAUGACUCUCCAUAGCCUUTT-3'

3) Target (SEQ ID NO: 9)
AAAGGCTATGGAGAGTCATCTGC

Sense-siRNA: (SEQ ID NO: 10)
5'-AGGCUAUGGAGAGUCAUCUTT-3'

Antisense-siRNA: (SEQ ID NO: 11)
5'-AGAUGACUCUCCAUAGCCUTT-3'

4) (SEQ ID NO: 12)
CAAGCAGTGTTCATTGGCCATGA

Sense-siRNA: (SEQ ID NO: 13)
5'-AGCAGUGUUCAUUGGCCAUTT-3'

Antisense-siRNA: (SEQ ID NO: 14)
5'-AUGGCCAAUGAACACUGCUTT-3'

5) (SEQ ID NO: 15)
CAGCACATGGAGGACTGGATTCC

Sense-siRNA: (SEQ ID NO: 16)
5'-GCACAUGGAGGACUGGAUUTT-3'

Antisense-siRNA: (SEQ ID NO: 17)
5'-AAUCCAGUCCUCCAUGUGCTT-3'

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash., found on the World Wide Web at oligoengine.com). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. And if you would like to attack the same targets by short hairpin RNAs, produced by a vector (permanent RNAi effect) you would put sense and antisense strand in a row with a loop forming sequence in between and suitable sequences for an adequate expression vector to both ends of the sequence. The ends of course depend on the cutting sites of the vector. The following are non-limiting examples of hairpin sequences that can be cloned into the pSuper vector:

1) Target: (SEQ ID NO: 19)
CAGTGTTCATTGGCCATGACTGG

-continued

Sense strand:
(SEQ ID NO: 20)
5'-GATCCCCGTGTTCATTGGCCATGACTTTCAAGAGAAGTCA
TGGCCAATGAACACTTTTT-3'

Antisense strand:
(SEQ ID NO: 21)
5'-AGCTAAAAAGTGTTCATTGGCCATGACTTCTCTTGAAA
GTCATGGCCAATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGATGACT
CTCCATAGCCTTTTTTT-3'

Antisense strand:
(SEQ ID NO: 24)
5'-AGCTAAAAAAAGGCTATGGAGAGTCATCTCTCTTGA
AGATGACTCTCCATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAGAA
GATGACTCTCCATAGCCTTTTTT-3'

Antisense strand:
(SEQ ID NO: 27)
5'-AGCTAAAAAAGGCTATGGAGAGTCATCATCTCTTGAA
AGATGACTCTCCATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAG
AGAATGGCCAATGAACACTGCTTTTTT-3'

Antisense strand:
(SEQ ID NO: 30)
5'-AGCTAAAAAAGCAGTGTTCATTGGCCATTCTCTT
GAAATGGCCAATGAACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAA
TCCAGTCCTCCATGTGCTTTTT-3'

Antisense strand:
(SEQ ID NO: 33)
5'-AGCTAAAAAGCACATGGAGGACTGGATTTCTCTTG
AAAATCCAGTCCTCCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, *J. Biol. Chem.* 263:15110; Ferrin and Camerini-Otero, 1991, *Science* 354:1494; Ramdas et al., 1989, *J. Biol. Chem.* 264: 17395; Strobel et al., 1991, *Science* 254:1639; and Rigas et al., 1986, *Proc. Natl. Acad. Sci. U.S.A.* 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10,000 nucleotides in length. Using this program with the sEH gene provides the following exemplar sequences:

1) UGUCCAGUGCCCACAGUCCU    (SEQ ID NO: 34)

2) UUCCCACCUGACACGACUCU    (SEQ ID NO: 35)

3) GUUCAGCCUCAGCCACUCCU    (SEQ ID NO: 36)

4) AGUCCUCCCGCUUCACAGA     (SEQ ID NO: 37)

5) GCCCACUUCCAGUUCCUUUCC   (SEQ ID NO: 38)

In another embodiment, ribozymes can be designed to cleave the mRNA at a desired position. (See, e.g., Cech, 1995, *Biotechnology* 13:323; and Edgington, 1992, *Biotechnology* 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired $T_m$). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, *Science* 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, 1996, *Current Opinion in Neurobiology* 6:629-634. Another subsequence, the h (hydrophobic) domain of signal peptides, was found to have similar cell membrane translocation characteristics (see, e.g., Lin et al., 1995, *J. Biol. Chem.* 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

VIII. Therapeutic Administration

Inhibitors of sEH and EETs can be prepared and administered in a wide variety of oral, parenteral and topical dosage forms. In preferred forms, compounds for use in the methods of the present invention can be administered by injection, that is, intravenously, intramuscularly, intracutaneously, subcutaneously, intraduodenally, or intraperitoneally. The sEH inhibitor or EETs, or both, can also be administered by inhalation, for example, intranasally. Additionally, the sEH inhibitors, or EETs, or both, can be administered transdermally. Accordingly, the methods of the invention permit administration of pharmaceutical compositions comprising a pharmaceutically acceptable carrier or excipient and either a selected inhibitor or a pharmaceutically acceptable salt of the inhibitor.

For preparing pharmaceutical compositions from sEH inhibitors, or EETs, or both, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of the sEH inhibitor, or EETs, or both, is employed in slowing or inhibiting nephropathy. The dosage of the specific compound for treatment depends on many factors that are well known to those skilled in the art. They include for example, the route of administration and the potency of the particular compound. An exemplary dose is from about 0.001 µM/kg to about 100 mg/kg body weight of the mammal.

EETs are unstable, and can be converted to DHET in acidic conditions, such as those in the stomach. To avoid this, EETs can be administered intravenously or by injection. EETs intended for oral administration can be encapsulated in a coating that protects the EETs during passage through the stomach. For example, the EETs can be provided with a so-called "enteric" coating, such as those used for some brands of aspirin, or embedded in a formulation. Such enteric coatings and formulations are well known in the art. In some formulations, the EETs, or a combination of the EETs and an sEH inhibitor are embedded in a slow-release formulation to facilitate administration of the agents over time.

Without further elaboration, it is believed that one skilled in the art can, using the preceding description, practice the present invention to its fullest extent.

EXAMPLES

Example 1

Urinary protein is usually a combination of albumin, globulins and minor components. Increased proteinuria (albuminuria) is associated with progressive kidney disease. The concentration of different urinary biomarkers responds to therapeutically relevant agents. Thus, the regular measurement of urinary albumin is a useful guide to the success of therapy in patients with many chronic renal diseases. Measurement of urinary albumin is often used in conjunction with measurements of other proteins and metabolic products, including serum and urine urea, creatinine, and ion concentrations, as well as serum C reactive protein, macroglobulin and various cytokines, in monitoring the progression of kidney damage.

The obese Zucker rat (OZR) is well known to rapidly develop numerous clinically relevant pathological conditions including, in addition to type 2 diabetes, hypertension and obesity, and spontaneous renal failure. E.g., Schmitz, P. G. et al., Sem. Nephr. 9(4), 354-369 (1989). The OZR is frequently used as an animal model for study of hypertension, renal function and diabetes. It has been demonstrated that, except for the final stages of end stage renal disease (by which time filtration is impaired and proteinuria/albuminuria actually decreases), urinary albumin is the single best indicator of renal failure in the OZR and that there is an almost linear increase in albumin from week 3 through week 18 in female OZRs.

Urinary albumin levels were studied as a function of oral treatment of OZR with the butyl ester of adamantyl urea dodecanoic acid ("AUDA") sEH inhibitor. The AUDA blood levels and urinary albumin were simultaneously monitored. While the female OZ rats were on the sEH inhibitor, there was no increase in urinary albumin. Discontinuing the treatment restored the preceding levels of urinary albumin.

Example 2

This Example provide exemplar assays for screening potential sEH inhibitors using affinity purified recombinant human, mouse and rat enzyme preparations.

Potential sEH inhibitors can be screened by high throughput bioassay methods incorporating recombinant mouse and human sEHs. To evaluate the relative potency of the inhibitors, $IC_{50}$ values are examined. The $IC_{50}$ is the concentration of inhibitor that reduces enzyme activity by 50%, and is typically determined by regression of at least five datum points with a minimum of two points in the linear region of the curve on either side of the $IC_{50}$. Conveniently, the curve is generated from several separate runs, each in triplicate, to obtain the standard deviation.

Enzyme preparation: Recombinant rat, mouse, pig, and human sEHs can be produced in a baculovirus expression system and purified by affinity chromatography, as taught in Grant et al., J Biol Chem, 268(23):17628-17633 (1993); Beetham et al., Arch. Biochem. Biophys., 305(1):197-201 (1993); and Wixtrom et al., Anal Biochem, 169(1):71-80 (1988). The purity can be judged by SDS-PAGE and scanning densitometry. These methods routinely provide enzymes that are at least 97% pure, and without detectable esterase or glutathione transferase activities, which can interfere with the sEH assay. Protein concentration can be quantified by using the Pierce BCA assay using Fraction V bovine serum albumin as the calibrating standard.

Determination of $IC_{50}$ values: $IC_{50}$ values can be assessed by using racemic 4-nitrophenyl-trans-2,3-epoxy-3-phenyl-propyl carbonate as substrate. Enzymes (0.1 µM mouse sEH or 0.20 µM human sEH) will be incubated with inhibitors for 5 min in sodium phosphate buffer, 0.1 M pH 7.4, containing 0.1 mg/mL of BSA, at 30° C. before substrate introduction ([S]=40 µM). Activity can be assessed by measuring the appearance of the 4-nitrophenolate anion at 405 nm at 30° C. during 1 min (Spectramax 340 PC; Molecular Devices).

Use LC/MS to determine the preliminary pharmacokinetics and effective dose: Pharmacokinetic properties of any particular sEH inhibitor can be tested in Wistar rats following oral or subcutaneous administration. Five microliters of blood are collected in a microcap from a small incision in the tail made using a child's lancet. The blood is mixed with 50 µL water, extracted with 100 µL of ethyl acetate, the solvent concentrated and analyzed by liquid chromatography ("LC")/mass spectroscopy ("MS") or MS. Standard pharmacokinetic parameters are determined.

Example 3

This Example sets forth exemplar assays for testing the ability of sEH inhibitors, or a combination of sEH inhibitors and EETs, to delay the onset of nephropathy in an animal model of diabetes.

Using analysis of blood and urine biomarkers determine if the onset of renal damage is delayed.

Obese Zucker rats ("OZR") are an autosomally recessive genetic model of obesity that is a commonly used model of relatively early onset human obesity. E.g., Farkas and Schlenker, Am. J. Respir. Crit. Care Med., 150(2):356-362 (1994). OZR are treated for 10 weeks with a known or potential sEH inhibitor (the "test agent"). To verify that effective levels of the test agent are maintained, the concentration of the test agent and indicator metabolites in blood and urine are monitored by LC-MS. Blood and urine samples are obtained once a week. Optionally, the kidneys are monitored in situ with high resolution ultrasound. Unlike mice, rats respond to vascular inflammation with high levels of C reactive protein which also increases linearly in the blood of OZR. This is monitored as an indication of vascular inflammation. Urinary albumin levels are measured as a marker of renal disease. Oxilipin levels, especially epoxides and diols of arachidonic and linoleic acids are determined by LC-MS. An increase in EETs should be associated with the expected decrease in renal damage. Spector et al., Prog. Lipid Res., 43:55-90 (2004).

Blood urea nitrogen, creatinine and other markers are monitored by LC-TOF. At monthly intervals creatinine clearance are determined. At the end of the period, renal pathology are be compared in treated and control OZR.

Animals. Female obese (24) and lean (8) Zucker rats are obtained. Animals are kept and maintained following classical animal protocols. For urine sampling, animals are housed in metabolic chamber for 24 h once a week. Urine is collected into insulated containers containing 5 mg each of triphenyl phosphine and butylated hydroxy toluene to prevent lipid autooxidation. Urinary albumin excretion is determined using electroimmuno-diffusion using rabbit anti-rat albumin and purified rat albumin, and C reactive protein in plasma is determined using a commercial ELISA. Blood samples (200 µl) are obtained from the tail vein once a week, treated with sodium EDTA, and centrifuged to isolate the plasma and red blood cells. All collected samples and fractions are stored frozen at −20° C. until analysis. Food and water intake are monitored. Blood levels of inhibitor and metabolites will be determined by LC-MS.

Example 4

This Example demonstrates a system for delivery of EETs using a wax plug.

Controlled release formulations have been one of the major focuses in pharmaceutics. Among the controlled release dosage forms, matrix-controlled release systems have been found to be convenient.

To create a wax pellet, wax was melted at 100° C. for 20 min using a hot plate. EETs were added to the molten wax while the wax was stirred. The wax-EETs suspension was poured into a mold made with glass plates and then cooled to room temperature. The resultant wax stick containing EETs was cut to suitable size.

To investigate release rate of EETs from wax pellets in vitro, a pellet (60 mg pellet containing 600 μg of EETs) in purified water (1 mL) containing an antioxidant was incubated at 37° C., and an aliquot (20 μL) of water was taken at various time intervals. Thirty μL of MeOH containing an internal standard was added to each aliquot and the mixture was subjected to LC-MS to determine the amount of any EETs in the aliquots.

To select suitable wax types and combinations of wax and helper substances such as lactose or coconut oil, a simplified test was developed using the drug lansoprazole. A wax pellet containing lansoprazole was made using the method described above with respect to forming pellets containing EETs.

To determine the release rate of lansoprazole from the wax pellets in vitro, a pellet (60 mg pellet containing 600 μg of lansoprazole) was incubated at 37° C. in 30 mL of purified water, and 1 mL aliquots of water were taken at various time intervals. The concentration of lansoprazole in the aliquot was determined by reading a spectrophotometer at 286 nm. The release rate of EETs from wax pellet can be determined in vivo by implanting the pellet under the skin of a mouse and collecting plasma and urine.

Example 5

This Example demonstrates a system for delivery of EETs using an enteric coating.

Enteric coatings are a useful method for the delivery of drugs that would be susceptible to degradation by stomach acid. Enteric coated EETs particles were tested.

The particle consisted of lactose, EETs and enteric coating polymer in the ratio of 2.0:0.1:0.4. Lactose powder was used as a core. To this core, EETs were added dropwise with mixing and then acetone or an EtOAC/EtOH solution of enteric coating polymer was added dropwise to the mixture. Drying in vacco gave enteric coated particles range in size from 200 to 360 nm, a suitable size powder for oral administration to mice and rats.

Dissolution tests were performed in (1) distilled water, (2) 0.1 M HCl solution (pH 3), and in a pH 7.4 phosphate buffer solution. Ten mg of the particle was added to each solution, which was then incubated at 37° C. The extracts were filtered with 0.2 μm nylon filter and extracted with 0.5 ml of EtOAc. After an internal standard was added, the solvent layers were evaporated with nitrogen gas and injected into a LC-MS. It was determined that, in the neutral pH buffer solution, the dissolved percentage of EETs from enteric coated particles was almost 100% after 10 min. In contrast, only 0.01% of EETs were found to be released into the acidic or water solutions. These results suggest release of EETs in enteric coated particles can pass through the stomach and delayed until the particle reach the slightly basic pH environment of the duodenum.

It is to be understood that while the invention has been described above in conjunction with preferred specific embodiments, the description and examples are intended to illustrate and not limit the scope of the invention, which is defined by the scope of the appended claims. All publications, sequences referred to in GenBank accession numbers, patents, and patent applications cited herein are hereby incorporated by reference for all purposes.

What is claimed is:

1. A method of inhibiting progression of nephropathy in:
   (a) a person with diabetes mellitus whose blood pressure is 130/80 or less, or (b) a person with metabolic syndrome whose blood pressure is less than 130/85,
   said method comprising administering an inhibitor of soluble epoxide hydrolase ("sEH") to said person, wherein the inhibitor of sEH comprises a urea, carbamate or amide pharmacophore.

2. A method of claim 1, wherein said inhibitor of sEH is selected from the group consisting of an isomer of adamantyl dodecyl urea, N-cyclohexyl-N'-dodecyl urea (CDU) and N,N'-dicyclohexylurea (DCU).

3. A method of claim 1, wherein the person has Type 2 diabetes.

4. A method of claim 1, wherein the person has Type 1 diabetes.

5. A method of claim 1, wherein the person has metabolic syndrome.

6. A method of claim 1, wherein the person has a triglyceride level over 215 mg/dL.

7. A method of claim 1, wherein the person has a cholesterol level over 200 mg/dL.

8. A method of claim 1, wherein the inhibitor of sEH is in a material which releases the inhibitor over time.

9. A method of claim 1, further comprising administering a cis-epoxyeicosantrienoic acid ("EET").

10. A method of claim 9, wherein said EET is selected from the group consisting of 14,15-EET, 8,9-EET and 11,12-EET.

11. A method of claim 9, wherein said EET is 14R,15S-EET.

12. A method of claim 9, wherein the EET is in a material which releases the EET into its surroundings over time.

13. A method of claim 1, wherein the inhibitor is administered orally.

14. A method as in claim 1, wherein the inhibitor is administered in a total daily dose from about 0.001 mg/kg to about 100 mg/kg body weight of the patient.

15. A method of claim 1, wherein the inhibitor of sEH inhibits sEH with an $IC_{50}$ of less than about 500 μM.

16. A method of inhibiting progression of nephropathy in a person in need thereof, said method comprising administering an inhibitor of soluble epoxide hydrolase ("sEH") to said person, wherein said inhibitor of sEH comprises a urea, carbamate or amide pharmacophore and inhibits sEH with an $IC_{50}$ of less than about 500 μM, wherein said person has blood pressure of 130/80 or less.

17. A method of claim 16, wherein said inhibitor of soluble epoxide hydrolase ("sEH") has a urea pharmacophore.

18. A method of claim 16, wherein the inhibitor of sEH is in a material which releases the inhibitor over time.

19. A method of claim 16, wherein the inhibitor is administered orally.

20. A method of claim 16, further comprising administering a cis-epoxyeicosantrienoic acid ("EET").

* * * * *